US00PP25590P3

(12) United States Plant Patent
Schoone

(10) Patent No.: US PP25,590 P3
(45) Date of Patent: May 26, 2015

(54) *PHALAENOPSIS* ORCHID PLANT NAMED 'WILDCAT'

(50) Latin Name: *Phalaenopsis hybrida*
Varietal Denomination: Wildcat

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 27 days.

(21) Appl. No.: 13/986,269

(22) Filed: Apr. 18, 2013

(65) Prior Publication Data

US 2013/0291242 P1 Oct. 31, 2013

Related U.S. Application Data

(60) Provisional application No. 61/638,237, filed on Apr. 25, 2012.

(51) Int. Cl.
*A01H 5/00* (2006.01)

(52) U.S. Cl.
USPC ..... Plt./311

(58) Field of Classification Search
CPC ..... A01H 5/02; A01H 5/00
USPC ..... Plt./311
See application file for complete search history.

*Primary Examiner* — June Hwu

(74) *Attorney, Agent, or Firm* — Foley & Lardner LLP; Sunit Talapatra

(57) ABSTRACT

A new and distinct *Phalaenopsis* plant named 'Wildcat' particularly characterized by flowers which are white with some yellow and some purple/red in the labellum; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'Wildcat'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Wildcat'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Wildcat' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Wildcat' originated from a cross made by the inventor in 1999 in Strengweg, Heemskerk, The Netherlands. The female or seed parent is the *Phalaenopsis* cultivar designated '(Hohoemi×Joseph Hampton×Taisuco Kaaladian)', unpatented. The male or pollen parent is the *Phalaenopsis* cultivar designated '(Malibu Real×amabilis)', unpatented. The new *Phalaenopsis* 'Wildcat' was discovered and selected by the inventor as a single flowering plant within the progeny of the stated cross in a controlled environment in 2007 in Strengweg, Heemskerk, The Netherlands.

Asexual reproduction of the new *Phalaenopsis* cultivar by tissue culture (mericloning) was first performed in November, 2007 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true to type.

BRIEF DESCRIPTION OF THE INVENTION

The following traits have been repeatedly observed and are determined to be unique characteristics of 'Wildcat', which in combination distinguish this *Phalaenopsis* as a new and distinct cultivar:

1. flowers which are white with some yellow and some purple/red in the labellum;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Wildcat', the flowers of the female parent '(Hohoemi×Joseph Hampton×Taisuco Kaaladian)' are about 11 cm high and the flowers of the male parent '(Malibu Real×amabilis)' are about 7 cm high, whereas the flowers of 'Wildcat' are about 9 cm high.

Presently, the commercial cultivar to which 'Wildcat' can be meaningfully compared is the *Phalaenopsis* orchid 'Telluride' (U.S. Plant Pat. No. 25,158). At the base of the lateral sepals of 'Telluride' is a vague yellow/green mark with red/purple spots. Whereas the lateral sepals of 'Wildcat' are white. Also, there is more yellow in the cirrhi of 'Telluride' than in the cirrhi of 'Wildcat'.

BRIEF DESCRIPTION OF THE PHOTOGRAPHS

The accompanying photographs illustrate the overall appearance of the new *Phalaenopsis* 'Wildcat' showing the colors as true as is reasonably possible with colored reproductions of this type. Colors in the photographs may differ slightly from the color values cited in the detailed botanical description, which accurately describe the color of 'Wildcat'.

DETAILED BOTANICAL DESCRIPTION

Figure 1:
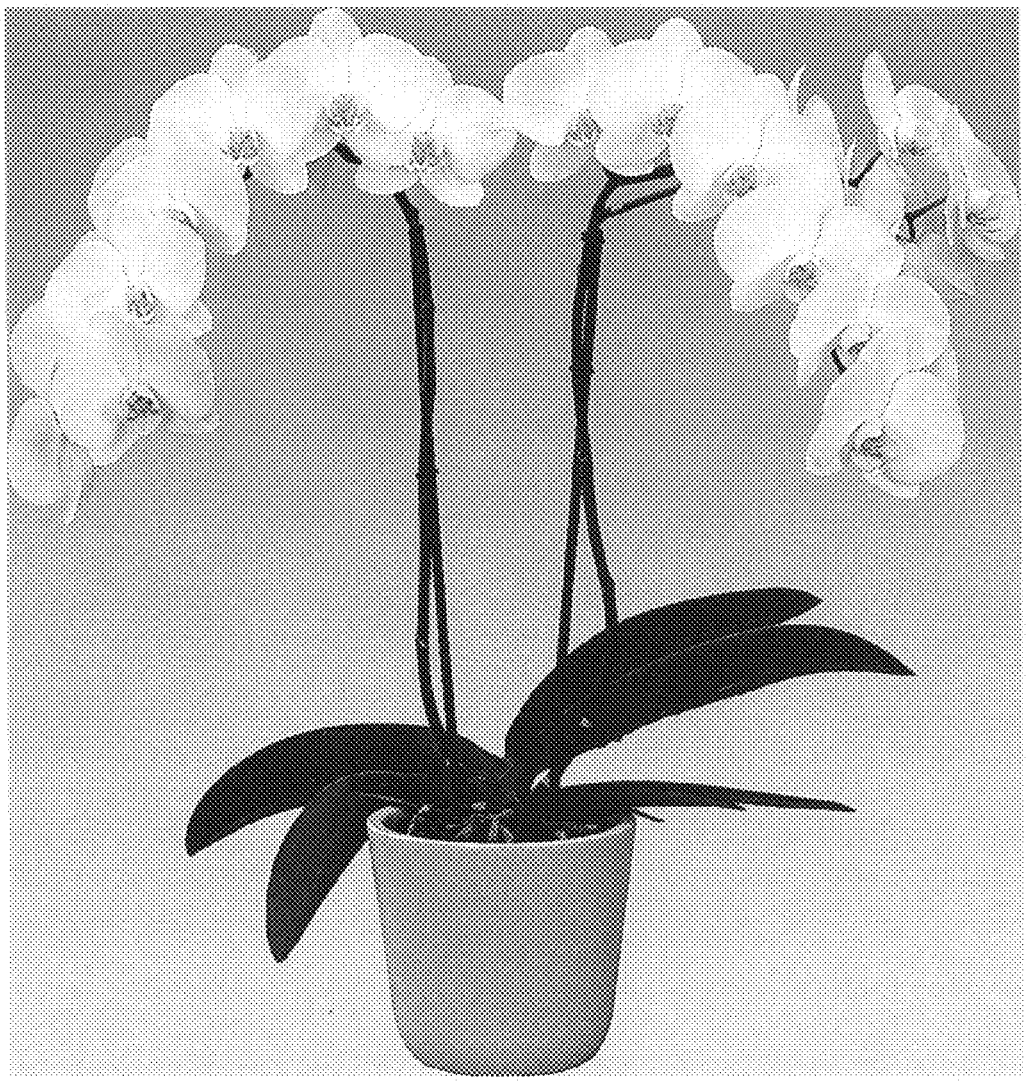
FIG. 1 shows a side view perspective of a typical flowering plant of 'Wildcat' in a 12 cm pot, at 16 months of age.

The new *Phalaenopsis* cultivar 'Wildcat' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Wildcat' as grown in a greenhouse in Strengweg, Heemskerk, The Netherlands, under conditions which closely approximate those generally used in commercial practice. Initially, the ideal temperature to grow plants of 'Wildcat' is 27° C. during the day and at night. Then, during the flowering phase of 'Wildcat', the ideal growing temperature is 20-22° C. during the day and 18° C. at night. Light levels for growing 'Wildcat' are a minimum of 5,000 lux and a maximum of 10,000 lux. A balanced fertilizer with level of 200 ppm N, 87 ppm P, 168 ppm K is applied. Duration of growth of 'Wildcat' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Wildcat' plants described is 12 months after potting.

Classification:

*Botanical.*—*Phalaenopsis hybrida.*

Parentage:

*Female or seed parent.*—*Phalaenopsis* cultivar designated '(Hohoemi×Joseph Hampton×Taisuco Kaaladian)', unpatented.

*Male or pollen parent.*—*Phalaenopsis* cultivar designated '(Malibu Real×amabilis)', unpatented.

Propagation:

*Type.*—Tissue culture (mericloning).

*Rooting habit and description.*—Fleshy; approximately 4 mm-6 mm wide and green in color (RHS 148C); freely branching. It takes 12 weeks for plants growing in tissue culture to initiate roots.

Plant:

*Size at maturity.*—Height (from bottom of pot to top of highest flower): about 60 cm. Spread: about 60 cm.

*Growth habit.*—Standard; green leaves (RHS 139A) and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 1 to 2 racemes with flowers appear.

Foliage:

*Quantity per plant.*—About 6 to 8 leaves are produced before flowering.

*Arrangement and attachment.*—Half up/horizontal and on two sides.

*Overall shape of leaf.*—Oval, narrow leaves, slightly point tip and asymmetric.

*Texture (upper & under side).*—Smooth and leathery.

*Pubescence.*—None.

*Mature leaf length.*—About 19 to 25 cm.

*Mature leaf width.*—About 6 to 8 mm.

*Mature leaf thickness.*—About 1 mm.

*Mature leaf color.*—Upper side: green (RHS 139A). Under side: green (RHS 137B).

*Leaf base.*—Acute.

*Margin.*—Entire.

*Venation.*—Pattern: parallel. Color of midvein: upper side: green (RHS N139A). under side: red/purple (RHS 138B).

Raceme:

*Quantity per plant.*—About 1 to 2.

*Number of flowers per raceme.*—About 9 to 12.

Peduncle:

*Length.*—About 54 to 57 cm.

*Diameter.*—About 4 to 6 mm.

*Strength.*—Strong.

*Aspect.*—Upright.

*Texture.*—Glabrous and smooth.

*Color.*—Green (RHS N139A) which runs into RHS 139B.

Inflorescence description:

*Appearance.*—Upright to slightly pendant, racemose inflorescence with bilaterally symmetrical flowers that open in succession beginning with the lowermost flower.

*Buds.*—Height (from base to tip): about 18 mm to 29 mm. Diameter (at midpoint): about 19 mm to 23 mm. Shape: egg-shaped. Color: yellow/green (RHS 154C) with a purple haze (RHS 76D) when almost opening and yellow/green (RHS 145A) with a purple haze (RHS 77B) on newest buds.

*Flowering time*.—For an untreated plant (flowering plant that has not undergone cold-treatment where the plant grows at a temperature of 18° C. to 19° C. for about 4 to 8 weeks after a period of about 30 weeks at a temperature of 25° C.), 1-2 racemes appear with flower buds and flowers. First flowers can be expected approximately 4 to 6 months after planting a plant with a leaf diameter of 3 to 5 cm. Flowers persistent.

*Flowering longevity*.—On the plant: about 4 to 6 months; lastingness of cut flowers: has not been observed.

*Fragrance*.—No fragrance.

Figure 2:
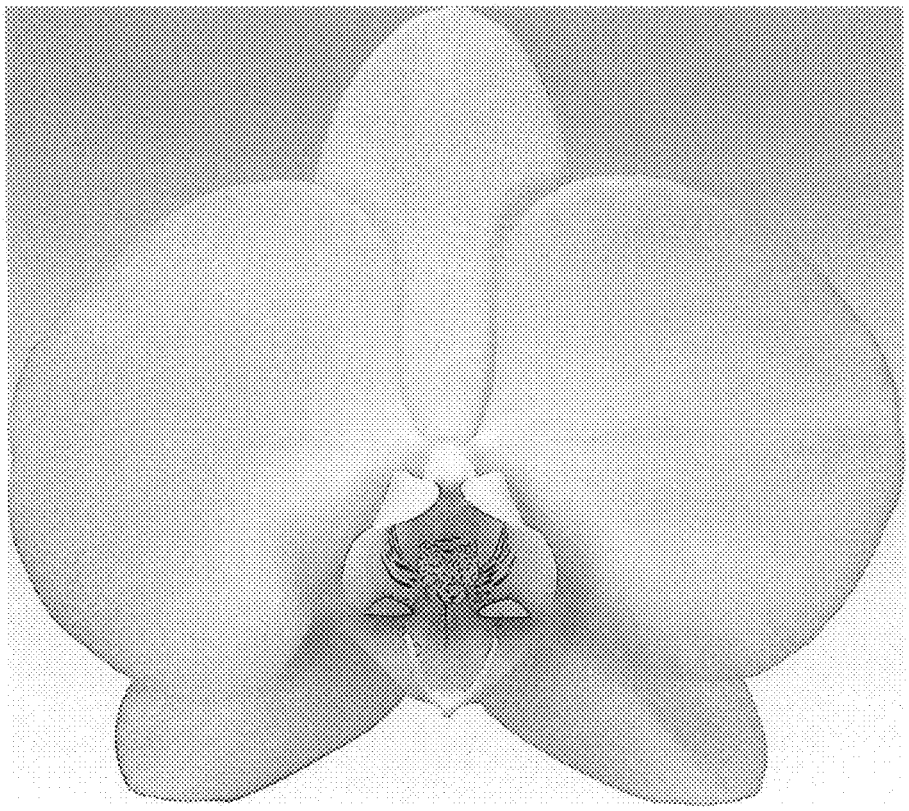
FIG. 2 shows a close-up view of the typical flower of 'Wildcat'.
Figure 3:
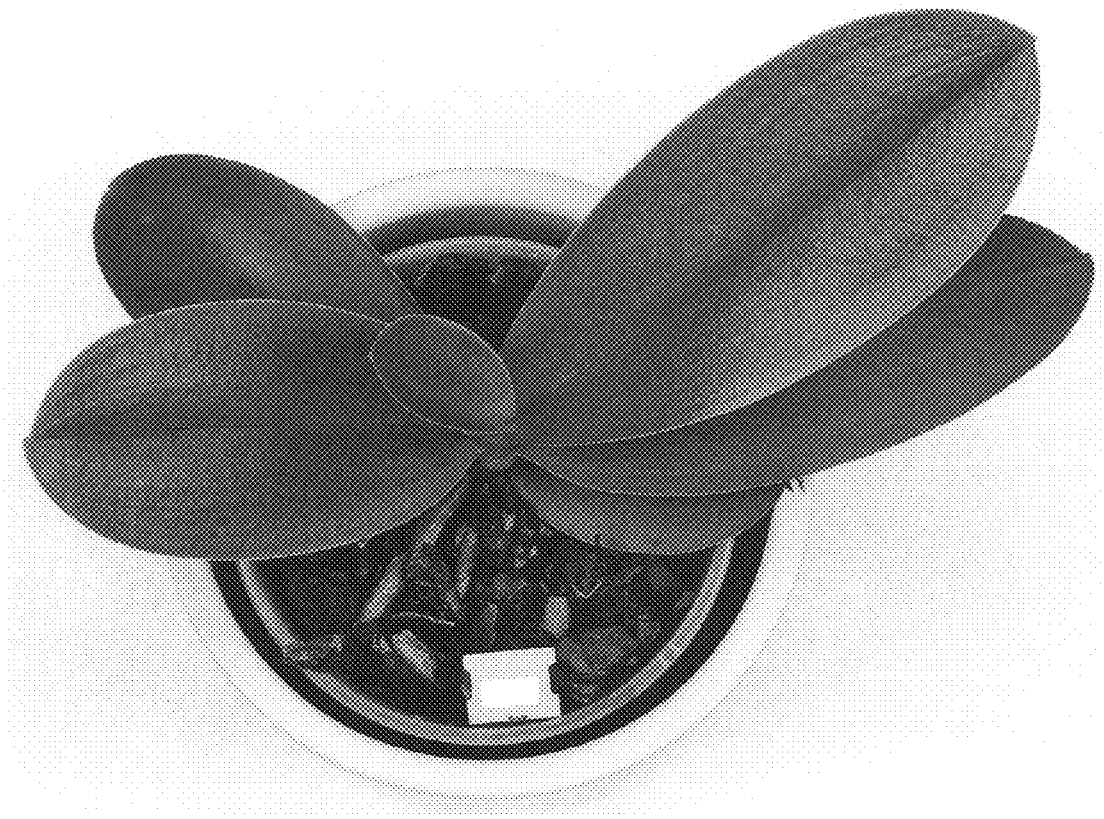
FIG. 3 shows a close-up view of the typical leaves of 'Wildcat'.

*Flower*.—Rate of opening: Flowers fully opened about 2 to 3 days after petal and sepal separation. Orientation at opening: slanted upward and outward. Shape: Typical shape of *Phalaenopsis* orchid; see FIG. 2. Size (of single bloom): Height: about 80 mm to 85 mm. Diameter: about 87 mm to 92 mm. Quantity and arrangement: three petals and three sepals, overlapping and arranged in 2 whorls. Petals are more pronounced than sepals.

*Petals*.—Arrangement: Inner whorl comprises 3 petals: 2 lateral petals and labellum. 2 lateral petals: Overall shape: broadly ovate and weakly cupped. Apex: oval with two little waves. Margin: entire and weakly undulate. Base: broadly ovate. Length: about 51 mm. Width: about 42 mm. Texture: Upper surface: smooth and satiny. Under surface: smooth and satiny. Color (when fully opened): upper side: white (RHS NN155C). Under side: white (RHS NN155C). Labellum: Overall shape: 3-lobed with 2 prominent callosities at central junction of the lateral lobes and base of the midlobe. Lateral lobes of labellum fold upward about the column; the midlobe extends forward and is terminated by 2 filiform appendages at the apex. Lateral lobes of the labellum are ovate in shape while the midlobe is triangular with a bump and a rib on it. Margin: entire and weakly undulate. Apex: oval. Length: about 21 mm. Width (not flattened): about 22 mm. Depth of tube (made from lateral lobes): about 14 mm. Texture: Upper and under surface: smooth and satiny. Color (when fully opened): Midlobe: upper surface: main color is white (RHS NN155C). On top in the corners yellow/green (RHS 154B). At the base a purple haze (RHS N78B) which runs through into the yellow/green in the corners. Line in the center yellow (RHS 3B) with purple/red stripes and spots (RHS 60A). Under surface: main color is white (RHS NN155C. At the base purple (RHS N78B) which runs in the corners into yellow/green (RHS 154B). Lateral lobes: upper surface: main color is white (RHS NN155C). On the edge yellow (RHS 3B/RHS 154C) and at the base red/purple stripes (RHS 60A). Under surface: main color is white (RHS NN155C). At the edge yellow (RHS 3B/RHS 154C) and at the base red/purple (RHS 60A). Cirrhi: long (about 20 mm) and curly. In between a little point color: white (RHS NN155C) with yellow tips (RHS 2B). Pestle (Callosities): Length: about 5 mm. Width (not flattened): about 6 mm. Color: main color is white (NN155C). Sides and top are yellow (RHS 7A) with red/purple stripes and spots (RHS 60A).

*Sepals*.—Arrangement: Outer whorl comprises 3 sepals. Overall shape: narrow, elliptical and weakly cupped. Margin: entire and weakly undulate. Length: about 43 mm. Width: about 28 mm. Apex: oval with a little point. Texture: Upper and under surface: smooth and satiny. Color (when fully opened): upper surface: dorsal & lateral: white (RHS NN155C). Under surface: dorsal & lateral: white (RHS NN155C).

*Pedicel*.—Length: about 34 mm. Diameter: about 4 mm. Texture: glabrous and smooth. Color: at the base yellow/green (RHS 146B), in the middle yellow/green (RHS 145C) and close to flower yellow/green (RHS 145D) with a purple haze (RHS 77D).

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Length: about 10 mm. Diameter: about 5 mm. Color: white (RHS NN155D).

*Pollinia*.—Quantity: two. Diameter: about 1 mm. Color: orange (RHS 24A).

*Ovary*.—Length: about 4 mm. Diameter: about 6 mm. Color: white (RHS NN155D), with sometimes a little bit of purple on the edges (RHS N80B).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Wildcat', as illustrated and described herein.

* * * * *

UNITED STATES PATENT AND TRADEMARK OFFICE

CERTIFICATE OF CORRECTION

PATENT NO. : PP25,590 P3
APPLICATION NO. : 13/986269
DATED : May 26, 2015
INVENTOR(S) : René Schoone It is certified that error appears in the above-identified patent and that said Letters Patent is hereby corrected as shown below:

ON THE TITLE PAGE, Item (30) insert:

-- (30) Foreign Application Priority Data

Apr. 26, 2012 (NL) .....OPS891 --.

Signed and Sealed this
Fifteenth Day of September, 2015

Michelle K. Lee

Michelle K. Lee
*Director of the United States Patent and Trademark Office*